(12) United States Patent
Penna et al.

(10) Patent No.: US 11,540,834 B2
(45) Date of Patent: *Jan. 3, 2023

(54) ANVIL ASSEMBLY WITH SNAP BACKUP RING

(71) Applicant: Covidien LP, Mansfield, MA (US)

(72) Inventors: Christopher Penna, Guilford, CT (US); Anthony Sgroi, Jr., Wallingford, CT (US); Steven Joyce, Durham, CT (US)

(73) Assignee: COVIDIEN LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/329,485

(22) Filed: May 25, 2021

(65) Prior Publication Data

US 2021/0275180 A1  Sep. 9, 2021

Related U.S. Application Data

(60) Division of application No. 16/171,498, filed on Oct. 26, 2018, now Pat. No. 11,013,514, which is a continuation of application No. 14/790,105, filed on Jul. 2, 2015, now Pat. No. 10,111,668.

(51) Int. Cl.
  *A61B 17/072* (2006.01)
  *A61B 17/115* (2006.01)
(52) U.S. Cl.
  CPC ........ *A61B 17/1155* (2013.01); *A61B 17/072* (2013.01); *A61B 17/115* (2013.01); *A61B 2017/07257* (2013.01)

(58) Field of Classification Search
  CPC ...... A61B 17/1155; A61B 2017/07257; A61B 2017/00473; A61B 2090/0814
  See application file for complete search history.

(56) References Cited

U.S. PATENT DOCUMENTS

| 3,193,165 | A | 7/1965 | Akhalaya et al. |
| 3,388,847 | A | 6/1968 | Kasulin et al. |
| 3,552,626 | A | 1/1971 | Astafiev et al. |
| 3,638,652 | A | 2/1972 | Kelley |
| 3,771,526 | A | 11/1973 | Rudie |
| 4,198,982 | A | 4/1980 | Fortner et al. |
| 4,207,898 | A | 6/1980 | Becht |
| 4,289,133 | A | 9/1981 | Rothfuss |

(Continued)

FOREIGN PATENT DOCUMENTS

| CA | 908529 A | 8/1972 |
| CN | 1907239 A | 2/2007 |

(Continued)

OTHER PUBLICATIONS

Japanese Office Action dated Mar. 18, 2020, issued in JP Appln. No. 2016125297 (no translation available).

(Continued)

*Primary Examiner* — Chelsea E Stinson
(74) *Attorney, Agent, or Firm* — Carter, Deluca & Farrell, LLP

(57) ABSTRACT

An anvil assembly is provided. The anvil assembly includes center rod assembly, a head assembly pivotal relative to the center rod assembly between an operative position and a tilted position, and a mechanism for selectively maintaining the head assembly in the operative position.

20 Claims, 11 Drawing Sheets

(56) References Cited

U.S. PATENT DOCUMENTS

| | | |
|---|---|---|
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshln et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |

(56) References Cited

U.S. PATENT DOCUMENTS

| | | |
|---|---|---|
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |

(56) References Cited

U.S. PATENT DOCUMENTS

| | | |
|---|---|---|
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 9,532,780 B2 * | 1/2017 | Williams ............ A61B 17/1155 |
| 9,554,802 B2 | 1/2017 | Williams et al. |
| 9,668,740 B2 | 6/2017 | Williams |
| 10,111,668 B2 | 10/2018 | Penna et al. |
| 11,013,514 B2 | 5/2021 | Penna et al. |
| 2003/0111507 A1 | 6/2003 | Nunez |
| 2004/0195289 A1 | 10/2004 | Aranyi |
| 2005/0006433 A1 | 1/2005 | Milliman et al. |
| 2005/0023325 A1 | 2/2005 | Gresham et al. |
| 2005/0051597 A1 | 3/2005 | Toledano |
| 2005/0107813 A1 | 5/2005 | Gilete Garcia |
| 2005/0116009 A1 | 6/2005 | Milliman |
| 2005/0205639 A1 | 9/2005 | Milliman |
| 2005/0205640 A1 | 9/2005 | Milliman |
| 2006/0000869 A1 | 1/2006 | Fontayne |
| 2006/0011698 A1 | 1/2006 | Okada et al. |
| 2006/0097025 A1 | 5/2006 | Milliman et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2008/0230581 A1 | 9/2008 | Marczyk et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0038401 A1 | 2/2010 | Milliman |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0211544 A1 | 8/2012 | Olson |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0092720 A1 | 4/2013 | Williams |
| 2013/0105544 A1 | 5/2013 | Mozdzierz et al. |
| 2013/0105546 A1 | 5/2013 | Milliman et al. |

(56) References Cited

U.S. PATENT DOCUMENTS

| | | |
|---|---|---|
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2014/0367450 A1 * | 12/2014 | Williams ............ A61B 17/115 227/181.1 |
| 2017/0000486 A1 | 1/2017 | Penna |
| 2017/0265857 A1 | 9/2017 | Williams |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 0698376 A2 | 2/1996 |
| EP | 1354560 A2 | 10/2003 |
| EP | 1857058 A1 | 11/2007 |
| EP | 2524656 A2 | 11/2012 |
| EP | 2583631 A1 | 4/2013 |
| EP | 2851011 A2 | 3/2015 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2015000346 A | 1/2015 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 0154594 A1 | 8/2001 |
| WO | 2008107918 A1 | 9/2008 |
| WO | 2014067829 A1 | 5/2014 |

OTHER PUBLICATIONS

European Search Report dated Nov. 3, 2016, issued in European Application No. 16177435.

Australian Examination Report dated Mar. 3, 2020, issued in AU Appln. No. 2016203732, 3 pages.

* cited by examiner

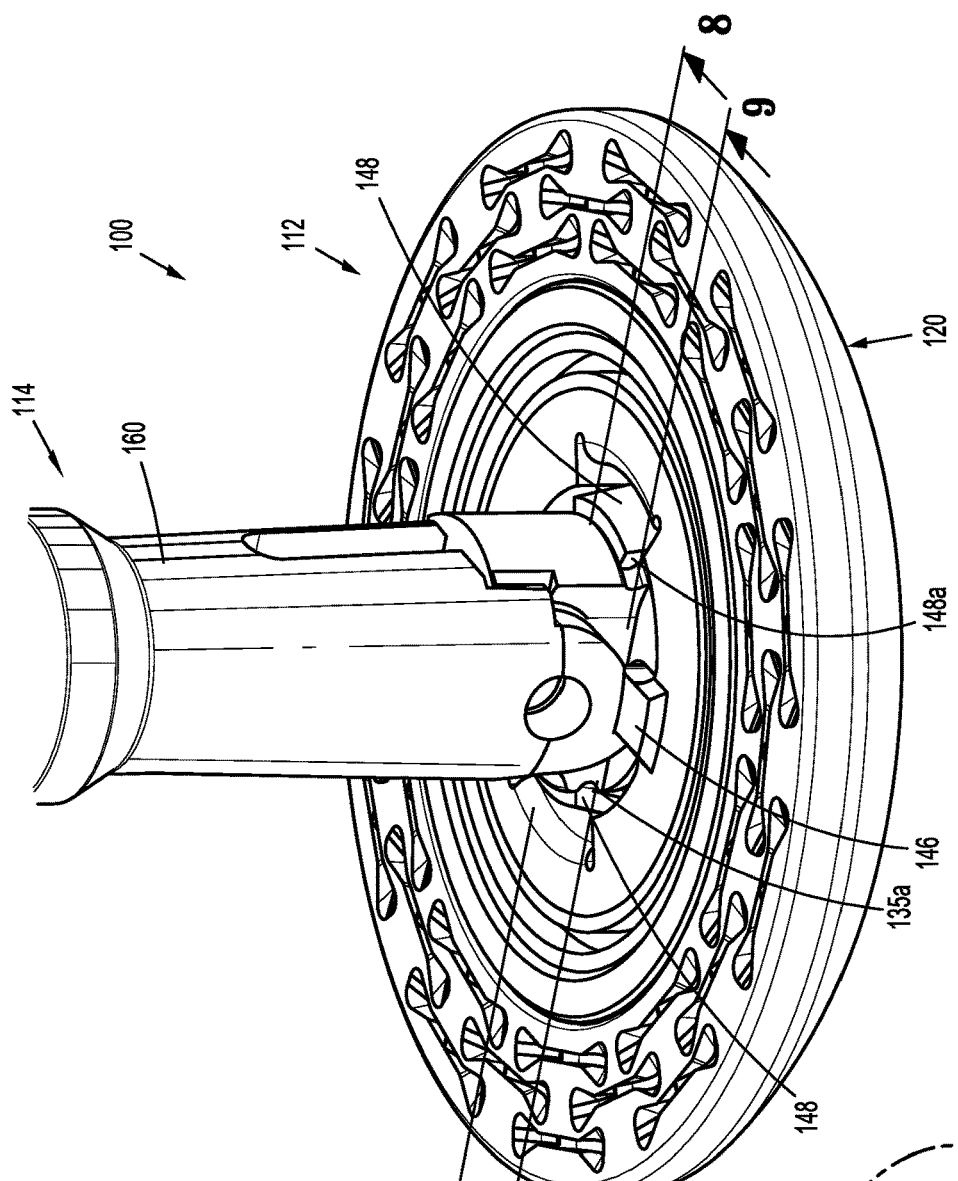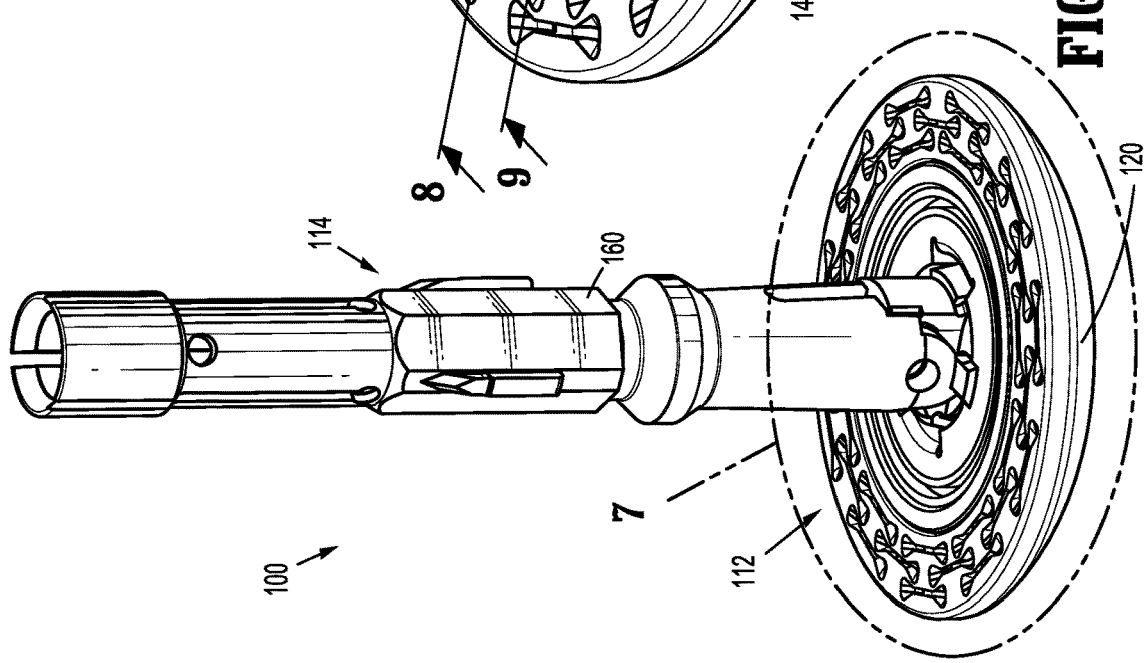

ANVIL ASSEMBLY WITH SNAP BACKUP RING

CROSS-REFERENCE TO RELATED APPLICATIONS

The present application is a Divisional Application of U.S. patent application Ser. No. 16/171,498, filed Oct. 26, 2018, which is a Continuation Application which claims that benefit of and priority to U.S. patent application Ser. No. 14/790,105, filed on Jul. 2, 2015, now U.S. Pat. No. 10,111,668, issued on Oct. 30, 2018, the entire content of which are incorporated herein by reference their entireties.

BACKGROUND

Technical Field

The present disclosure relates generally to an anvil assembly having a tiltable head which is suitable for use with a circular anastomosis stapler. More specifically, the present disclosure relates a tiltable anvil assembly having an improved retaining mechanism. Background of Related Art Circular anastomosis staplers which include an anvil assembly having a tiltable anvil head are known in the art. An example of such circular anastomosis stapler and tiltable anvil assembly are disclosed in commonly owned U.S. Pat. No. 7,364,060 ("the '060 patent"). A further example of a tiltable anvil assembly is disclosed in commonly owned U.S. Pat. No. 8,540,132 ("the '132 patent"). The content of each of the '060 patent and the '132 patent are incorporated herein by reference in their entirety. The anvil assembly described in the '132 patent includes a backup member located within the anvil assembly positioned to prevent tilting of the anvil head of the anvil assembly prior to firing of the stapler, e.g., in a proximal position. Upon firing of the stapler, a knife blade of the stapler engages and moves the backup member to a position, e.g., a distal position, which allows the anvil head to tilt upon retraction of the knife blade. If the backup member sticks to the knife blade upon retraction of the knife blade and/or is otherwise not retained in the distal position, the backup member may return to the proximal position, thereby preventing the anvil head from tilting.

In order to maintain the backup member in the proximal position where it prevents tilting of the anvil head prior to firing, the anvil assembly described in the '132 patent includes a retainer member positioned distal of the backup member. The retainer member includes a plurality of deformable tabs which prevent distal movement of the backup member until a predetermined force sufficient to deform the tabs is applied to the backup member, i.e., through engagement with the knife blade during staple formation. A residual proximal force is produced during deformation of the deformable tabs. This force acts on the backup member which may cause the backup member to move proximally towards its original position. As described in the '132 patent, the tilting operation of the anvil assembly relies on the distal positioning of the backup member following the firing of the stapler. Any proximal force that acts on the backup member may cause the backup member to return to the original proximal position, thereby preventing tilting of the anvil assembly.

Therefore, it would be beneficial to provide an anvil assembly with a mechanism or feature for retaining the backup member in the proximal position prior to firing of the stapling assembly, that allows the backup member to move to the distal position during firing of the stapling assembly, and that retains the backup member in the distal position after firing of the stapling assembly such that the anvil assembly may tilt.

SUMMARY

Accordingly, an anvil assembly is provided. The anvil assembly includes a center rod assembly and a head assembly pivotally supported on the center rod assembly between an operative position and a tilted position. The head assembly includes a housing, a post extending proximally from the housing and defining a proximal annular groove, and a backup member operably supported about the post, wherein the backup member is movable from a first position in which a portion of the backup member is positioned to prevent pivotal movement of the head assembly from the operative position to the tilted position, to a second position in which the backup member is positioned to permit pivotal movement of the head assembly from the operative position to a tilted position. The backup member includes a first locking feature and a second locking feature receivable within the proximal annular groove of the post to maintain the backup member in the first position.

In embodiments, the post further defines a distal annular groove, the first and second locking features being received within the distal annular groove to maintain the backup member in the second position. The center rod assembly may include a center rod having at least one tab. The at least one tab may engage the backup member when the backup member is in the first position to maintain the head assembly in the operative position. Movement of the backup member from the first position to the second position may disengage the backup member from the at least one tab to permit the head assembly to move to the tilted position.

The first and second locking features may be configured to prevent movement of the backup member from the first position to the second position until a predetermined force has been applied to the backup member. The first and second locking features may be configured to flex radially outward when the predetermined force is applied to the backup member. The first and second locking features may each include a ridge configured for receipt within the proximal annular groove when the backup member is in the first position and within the distal annular groove when the backup member is in the second position.

In embodiments, an anvil assembly in accordance with the present disclosure includes a center rod assembly, and a head assembly pivotally supported on the center rod assembly between an operative position and a tilted position. The head assembly includes a housing, a post extending proximally from the housing, and a backup member operably supported about the post, wherein the backup member is movable from a first position in which a portion of the backup member is positioned to prevent pivotal movement of the head assembly from the operative position to the tilted position, to a second position in which the backup member is positioned to permit pivotal movement of the head assembly from a operative position to the tilted position. The backup member includes a first detent and a second detent configured to engage a proximal surface of the post to maintain the backup member in the first position.

In embodiments, the post defines first and second cutouts for receiving the respective first and second detents when the backup member is in the second position. The center rod assembly may include a center rod having at least one tab, wherein the at least one tab engages the backup member when the backup member is in the first position to maintain the head assembly in the operative position. Movement of the backup member from the first position to the second position may disengage the backup member from the at least one tab to permit the head assembly to move to the tilted position. The at least one tab may engage one of the first and second detents. The first and second detents may be configured to prevent movement of the backup member from the first position to the second position until a predetermined force has been applied to the backup member.

BRIEF DESCRIPTION OF THE DRAWINGS

Various embodiments of the presently disclosed anvil assembly are disclosed herein with reference to the drawings wherein:

FIG. 6 is a perspective side view of the anvil assembly shown in FIG. 4;

FIG. 7 is an enlarged view of the indicated area of detail shown in FIG. 6;

DETAILED DESCRIPTION OF EMBODIMENTS

Figure 1:
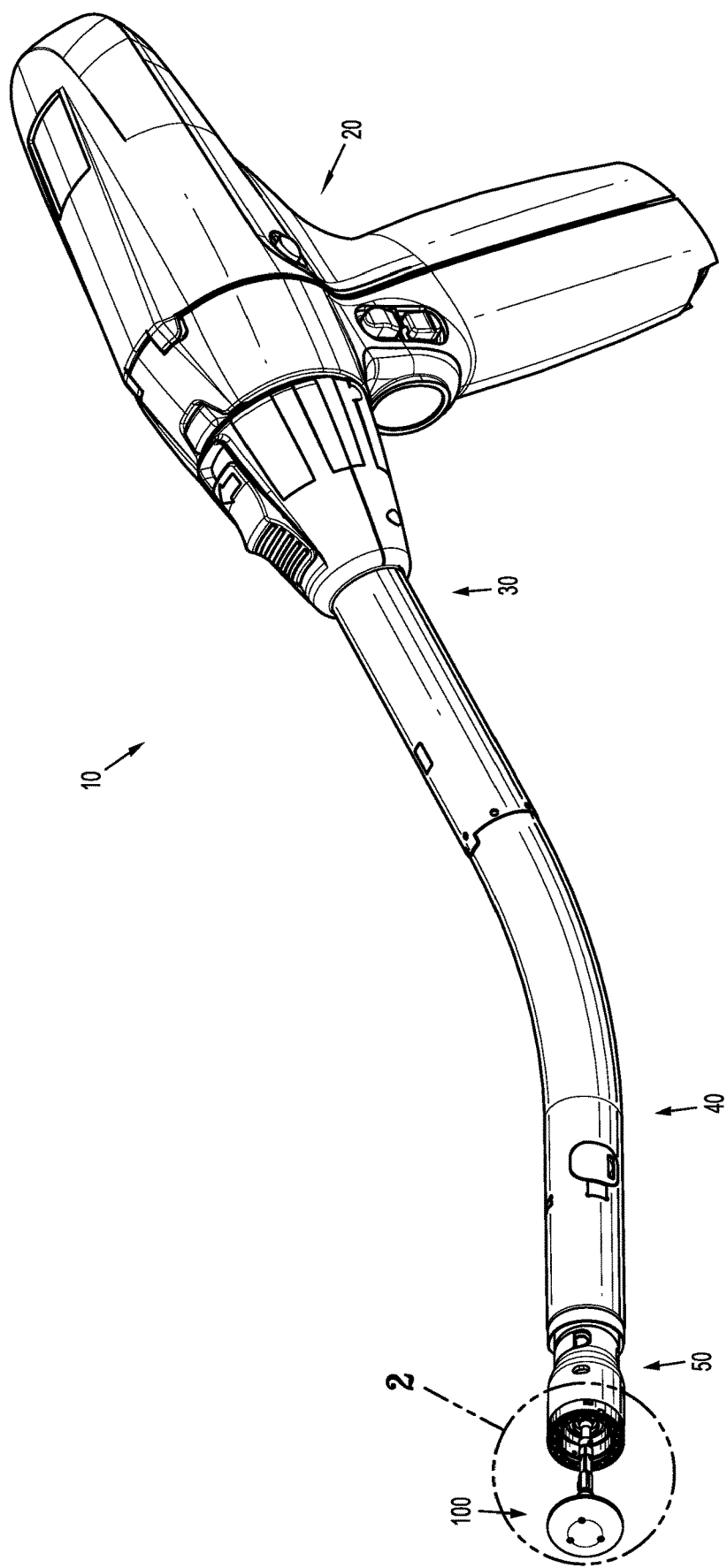
FIG. 1 is a perspective side view of a surgical stapling device including an embodiment of an anvil assembly according to the present disclosure.

Embodiments of the presently disclosed anvil assembly will now be described in detail with reference to the drawings in which like reference numerals designate identical or corresponding elements in each of the several views. As is common in the art, the term "proximal" refers to that part or component closer to the user or operator, i.e. surgeon or clinician, while the term "distal" refers to that part or component further away from the user.

Figure 2:
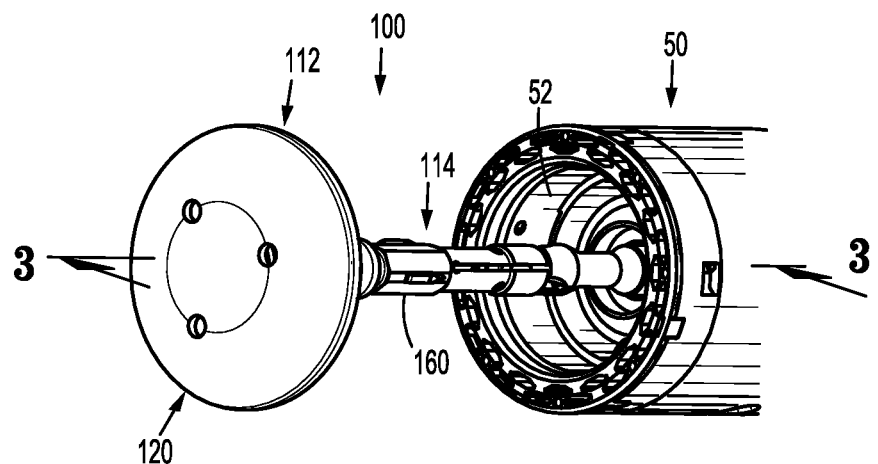
FIG. 2 is enlarged view of the indicated area of detail shown in FIG. 1.
Figure 3:
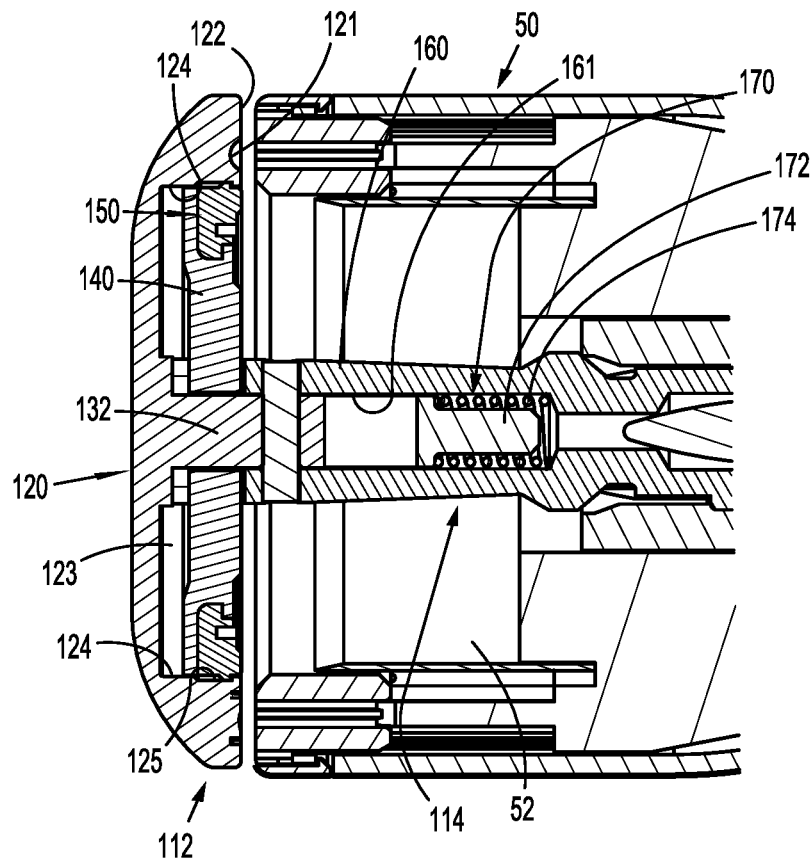
FIG. 3 is a cross-sectional side view taken along line 3-3 shown in FIG. 2, illustrating the anvil assembly approximated against a loading unit.

Referring initially to FIGS. 1-3, an anvil assembly according to an embodiment of the present disclosure, shown generally as anvil assembly 100, is secured to a surgical stapling device 10. The surgical stapling device 10 includes a powered handle 20, an adapter assembly 30, an extension assembly 40, and a loading unit 50. Although shown and described with reference to anvil assembly 100 and surgical stapling device 10, the aspects of the present disclosure may be modified for use with anvil assemblies having alternative configurations, with manual surgical stapling devices having various configurations, and with powered surgical stapling devices having alternative configurations. For a detailed description of an exemplary surgical stapling device, please refer to commonly owned U.S. Pat. No. 9,023,014 ("the '014 patent) and U.S. Pat. Appl. Publ. No. 2012/0253329 ("the '329 application"), the contents of which are incorporated by reference herein in their entirety.

Figure 4:
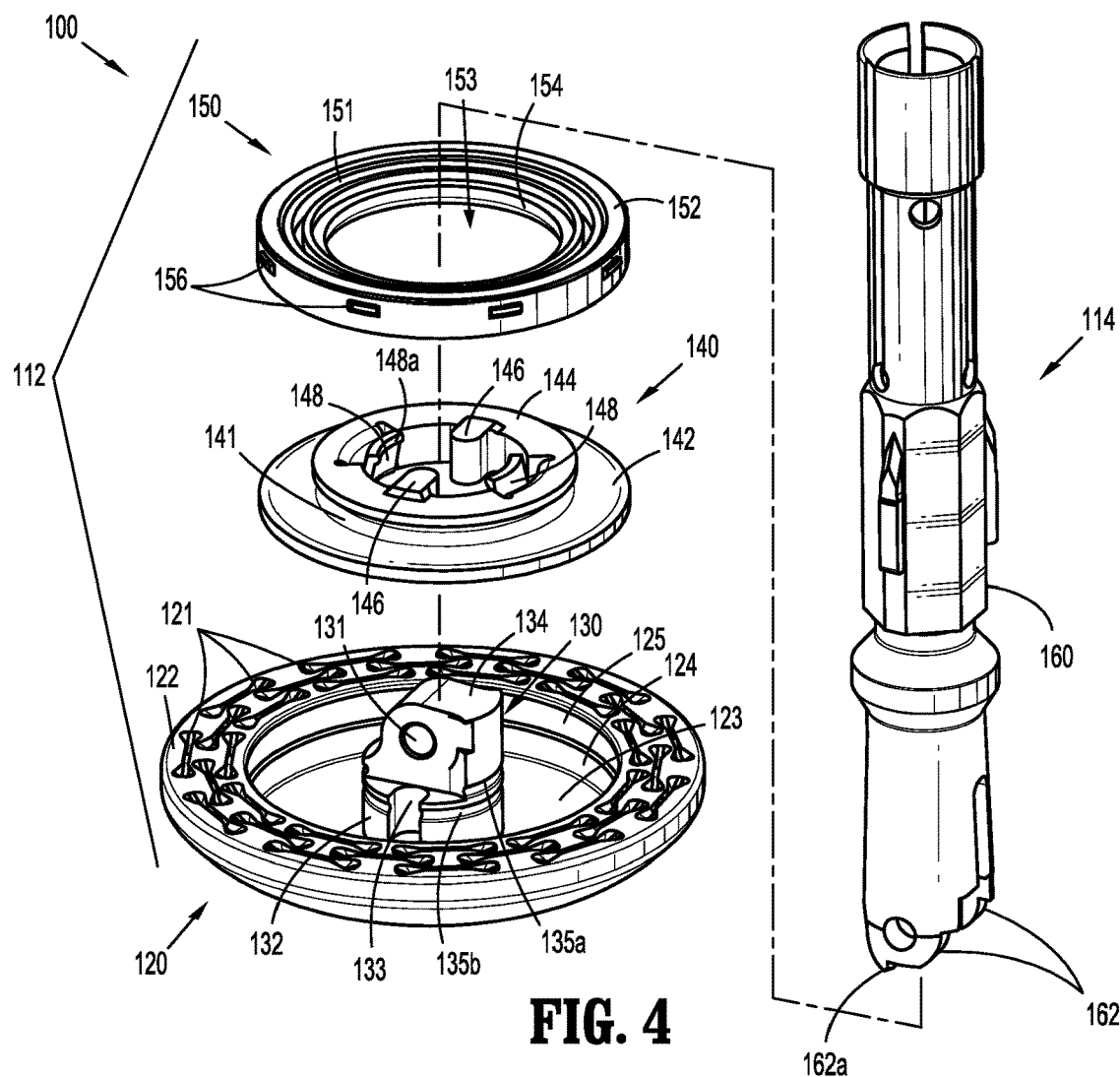
FIG. 4 is a perspective side view of the anvil assembly shown in FIG. 1 with the parts separated.
Figure 11:
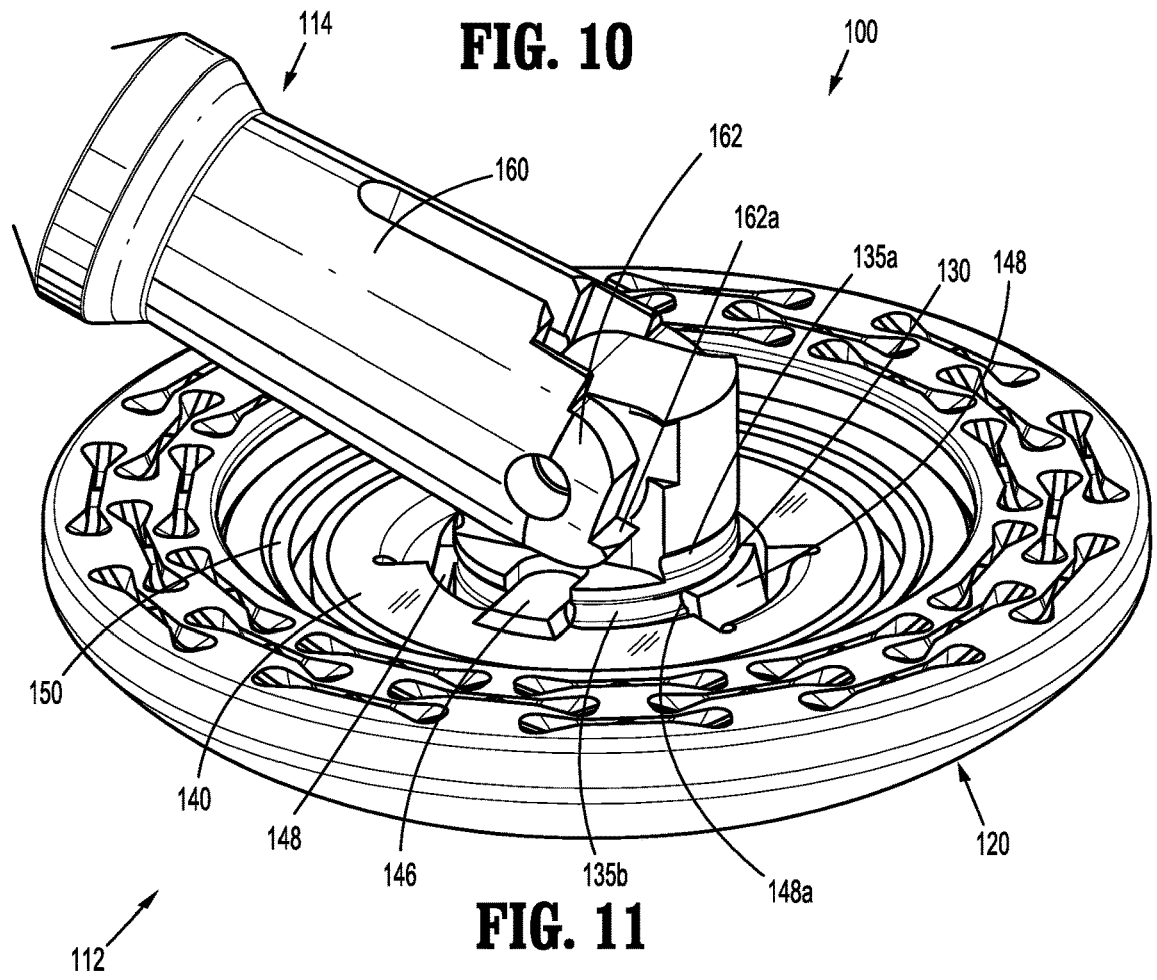
FIG. 11 is a perspective top view of a head assembly of the anvil assembly shown in FIG. 4 subsequent to firing of the surgical stapling device show in FIG. 1.

Referring to FIGS. 2-4, briefly, the anvil assembly 100 includes a head assembly 112 pivotally secured to a center rod assembly 114. The head assembly 112 includes a housing 120, a post 130, a backup member 140, and a cutting ring 150. The center rod assembly 114 includes a center rod 160 and a biasing mechanism 170 (FIG. 3) operably received within a distal bore 161 (FIG. 3) of the center rod 160. The biasing mechanism 170 facilitates moving of the head assembly 112 relative to the center rod 160 between at least an operative position (FIG. 6) and a tilted position (FIG. 11). The biasing mechanism 170 includes a plunger member 172 (FIG. 3) and a biasing member, e.g., a compression spring 174 (FIG. 3). For a detailed description of an exemplary center rod assembly 114, please refer to the '132 patent, the contents of which were previously incorporated by reference herein.

With continued reference to FIGS. 3 and 4, the housing 120 of the head assembly 112 of the anvil assembly 100 defines a plurality of staple forming pockets 121 on a proximal facing surface 122 thereof. Alternatively, the head assembly 112 may include an anvil plate (not shown), defining a plurality of staple forming pockets (not shown), supported on the proximal facing surface 122 of the housing 120. The housing 120 further defines a cavity 123 between an inner wall 124 and the post 130 for operably receiving the backup member 140 and the cutting ring 150. As will be described in further detail below, the inner wall 124 of the housing 120 defines an annular groove 125 for receiving a plurality of tabs 156 of the cutting ring 150.

As shown, the post 130 of the head assembly 112 is monolithically formed with and centrally positioned within the housing 120. Alternately, the housing 120 and the post 130 are formed separately and fastened together using a known fastening technique, e.g., adhesive, welding, friction fit, etc. The post 130 includes a substantially cylindrical body 132 having a projection 134, and defining opposed cutouts 133 and proximal and distal annular grooves 135a, 135b. The projection 134 of the post 130 defines a throughbore 131 and is configured to operably engage the center rod 160 of the center rod assembly 114. More particularly, the projection 134 of post 130 is received between extensions 162 of the center rod 160 of the center rod assembly 114 and is pivotally secured to the center rod 160 by a pivot pin 162 received through the throughbore 131.

Figure 5:
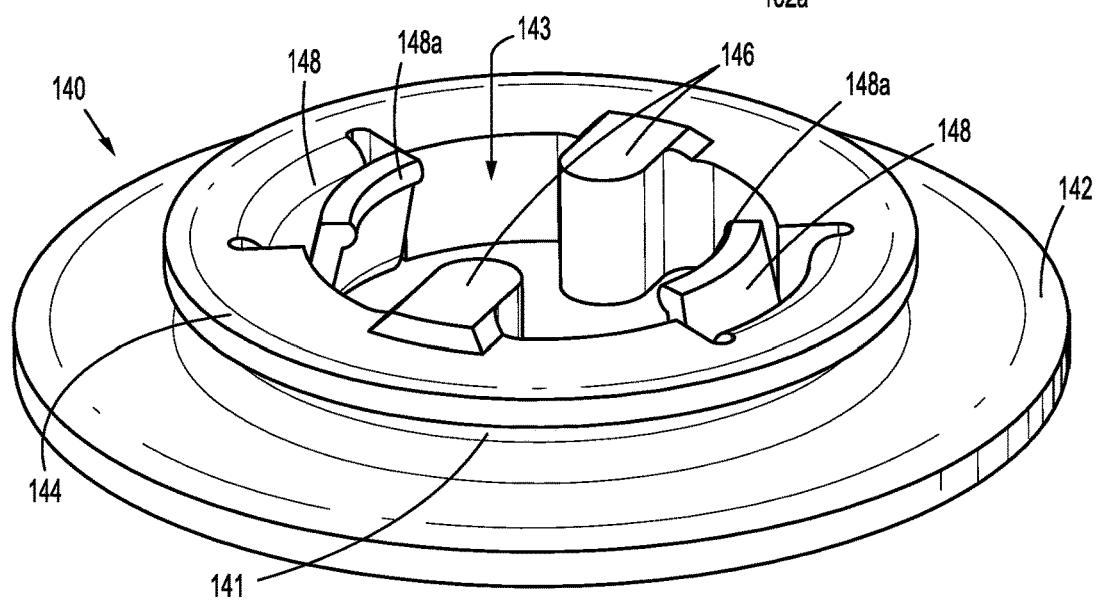
FIG. 5 is a perspective side view of a backup member of the anvil assembly shown in FIG. 4.
Figure 8:
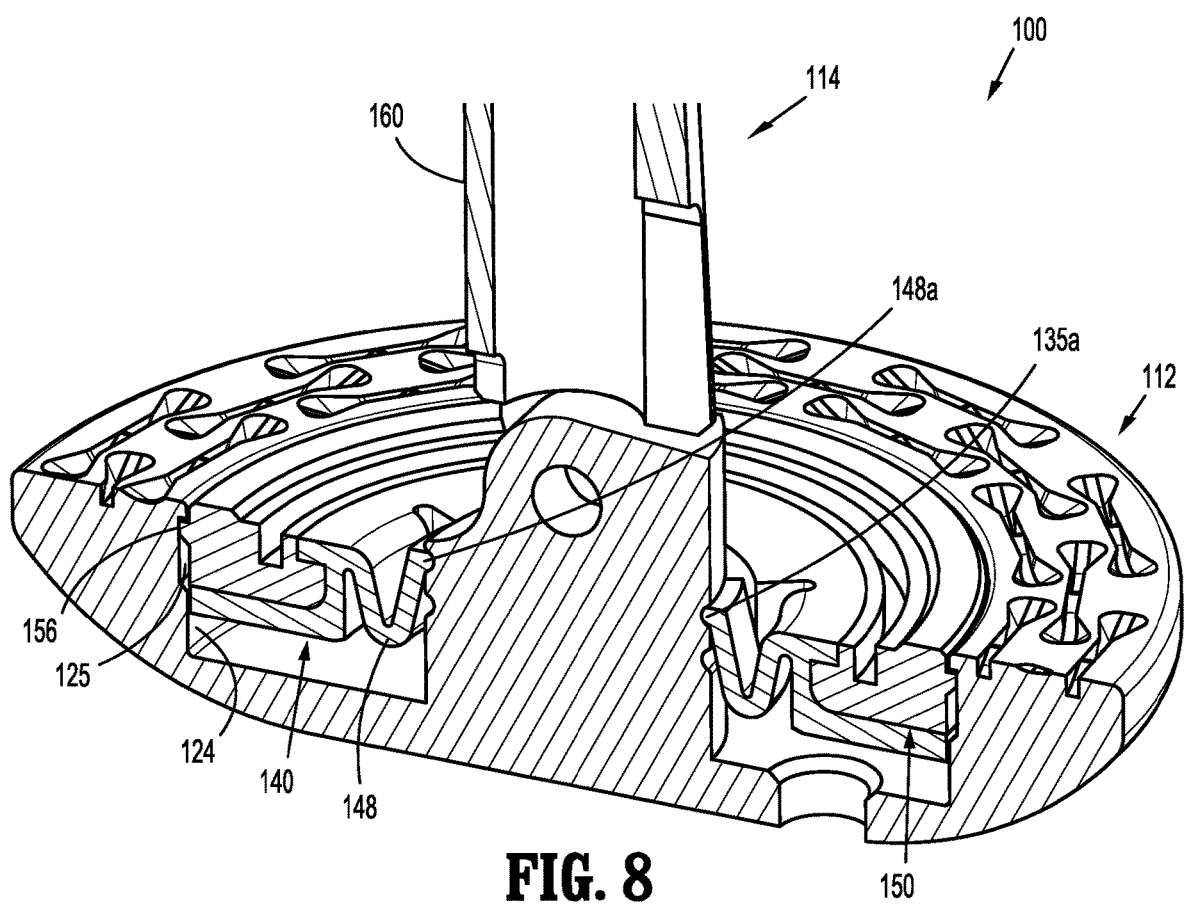
FIG. 8 is a cross-sectional perspective view taken along line 8-8 shown in FIG. 7.
Figure 9:
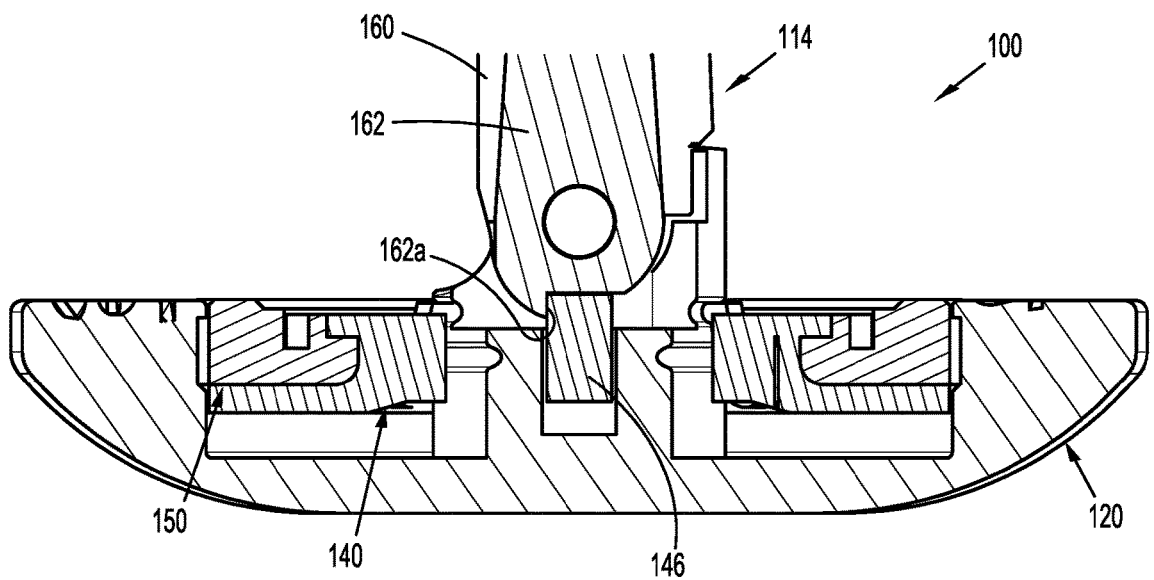
FIG. 9 is a cross-sectional side view taken along line 9-9 shown in FIG. 7.

With additional reference to FIG. 5, the backup member 140 of the head assembly 112 includes an annular body 142 and an annular flange 144 extending from the annular body 142. The backup member 140 defines an annular groove 141 disposed between the annular body 142 and the annular flange 144, and a central opening 143 extending through the annular body 142 and the annular flange 144. The backup member 140 is operably receivable within the cavity 123 of the housing 120 of the head assembly 112 about the post 130. The backup member 140 includes opposed protrusions 146 extending within the central opening 143 and receivable within the opposed cutouts 133 of the post 130 when the backup member 140 is received within the cavity 123 of the housing 120. As will be described in further detail below, when the backup member 140 is in a proximal position (FIG. 3), the opposed protrusions 146 engage tabs 162a formed on the extensions 162 of the center rod 160 of the center rod assembly 114 to maintain the head assembly 112 in an operative position (FIG. 3).

With particular reference still to FIG. 5, the backup member 140 further includes opposed locking features 148 that frictionally engage the post 130 when the backup member 140 is received within the cavity 121 of the housing 120 and about the post 130. More particularly, each of the opposed locking features 148 forms a resilient member that includes a ridge 148a selectively receivable within the proximal and distal annular grooves 135a, 135b of the post 130. When the ridges 148a of the opposed locking features 148 of the backup member 140 are received within the proximal annular groove 135a of the post 130, the opposed locking features 148 operate to maintain the backup member 140 in the proximal position (FIG. 3). Although shown including two locking features 148, it is envisioned that the backup member 140 may include three (3) or more locking features 148.

When a predetermined force is applied to the backup member 140 in the distal direction, the opposed locking features 148 of the backup member 140 are configured to flex radially outwardly as the backup member 140 moves in a distal direction. The radial outward flexion of the ridges 148a of the opposed locking features 148 retract the ridges 148a from within the proximal annular groove 135a, thereby permitting continued distal movement of the backup member 140. The distal annular groove 135b of the post 130 is positioned such that when the backup member 140 is moved to the distal position (FIG. 13), the ridges 148a of the opposed locking features 148 align with and are subsequently received within the distal annular groove 135b because of the resilient nature of the opposed locking features 148.

With continued reference to FIGS. 3 and 4, the cutting ring 150 of the head assembly 112 of the anvil assembly 100 includes an annular body 152 and defines an annular groove 151 and a central opening 153. The cutting ring 150 is secured about the annular flange 144 of the backup member 140 and includes an inwardly extending lip 154 that is received within the annular groove 143 of the backup member 140 for securing the cutting ring 150 to the backup member 140. As noted above, a plurality of tabs 156 extend outwardly from the annular body 152 of the cutting ring 150. The plurality of tabs 156 are received within the annular groove 125 formed in the inner wall 124 of the housing 120 when the cutting ring 150 is received within the cavity 123 of the housing 120. The plurality of tabs 156 maintains the backup member 140 and the cutting ring 150 within the housing 120 of the head assembly 112.

Although the cutting ring 150 is shown and described as being formed as an independent component that is secured to the backup member 140 by placing the cutting ring 150 around the annular flange 144 of the backup member 140 and receiving the lip 154 of the cutting ring 150 within the annular groove 143 of the backup member 140, it is envisioned that the backup member 140 and the cutting ring 150 may be integrally formed, or formed as a one piece or monolithic structure.

With reference now to FIGS. 6-9, the anvil assembly 100 is shown with the head assembly 112 in the operative position. In the operative position, the backup member 140 and the cutting ring 150 are in the proximal position. When the backup member 140 and the cutting ring 150 are in the proximal position, the ridges 148a of the opposed locking features 148 of the backup member 140 are received within the proximal annular groove 135a of the post 130 to maintain the backup member 140 and the cutting ring 150 in the proximal position. Additionally, the plurality of tabs 156 (FIG. 8) of the cutting ring 150 are received within the annular groove 125 formed in the inner surface 124 of the housing 120 to maintain the backup member 140 and the cutting ring 150 within the cavity 123 of the housing 120.

As noted above, the head assembly 112 of the anvil assembly 100 is maintained in the operative position by the backup member 140 when the backup member 140 is in the proximal position. In particular, the opposed protrusions 146 of the backup member 140 engage the tabs 162a extending from the extension 162 of the center rod 160 of the center rod assembly 114 to prevent the head assembly 112 from pivoting to the tilted position (FIG. 11) relative to the center rod 160.

Figure 10:
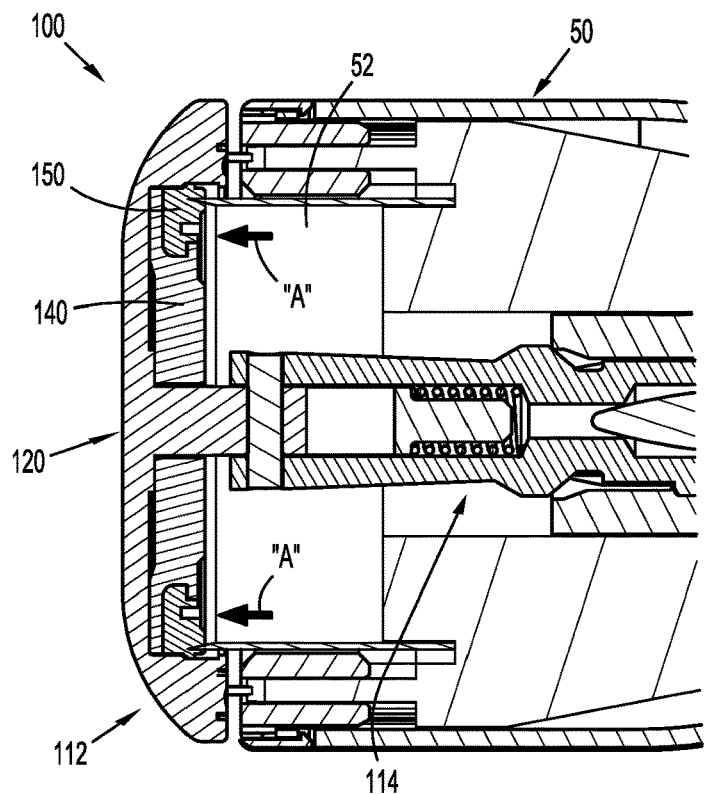
FIG. 10 is a cross-sectional side view taken along line 3-3 shown in FIG. 2, during a tissue cutting stroke.

With reference now to FIG. 10, during actuation of surgical stapling device 10, subsequent to the stapling of tissue in a two stroke stapling device, or concurrently with the stapling of tissue in a single stroke device, the knife 52 of the loading unit 50 is advanced into contact with the cutting ring 150 of the head assembly 112 of the anvil assembly 100. Since the cutting ring 150 is secured to the backup member 140, the force applied to the cutting ring 150 is transferred to the backup member 150. As noted above, when the predetermined force is applied to the backup member 140, the opposed locking features 148 of the backup member 140 flex radially outwardly to retract the ridges 148a of the opposed locking features 148 from within the proximal annular groove 135a of the post 130 to allow the backup member 140 to move relative to the post 130.

Figure 12:
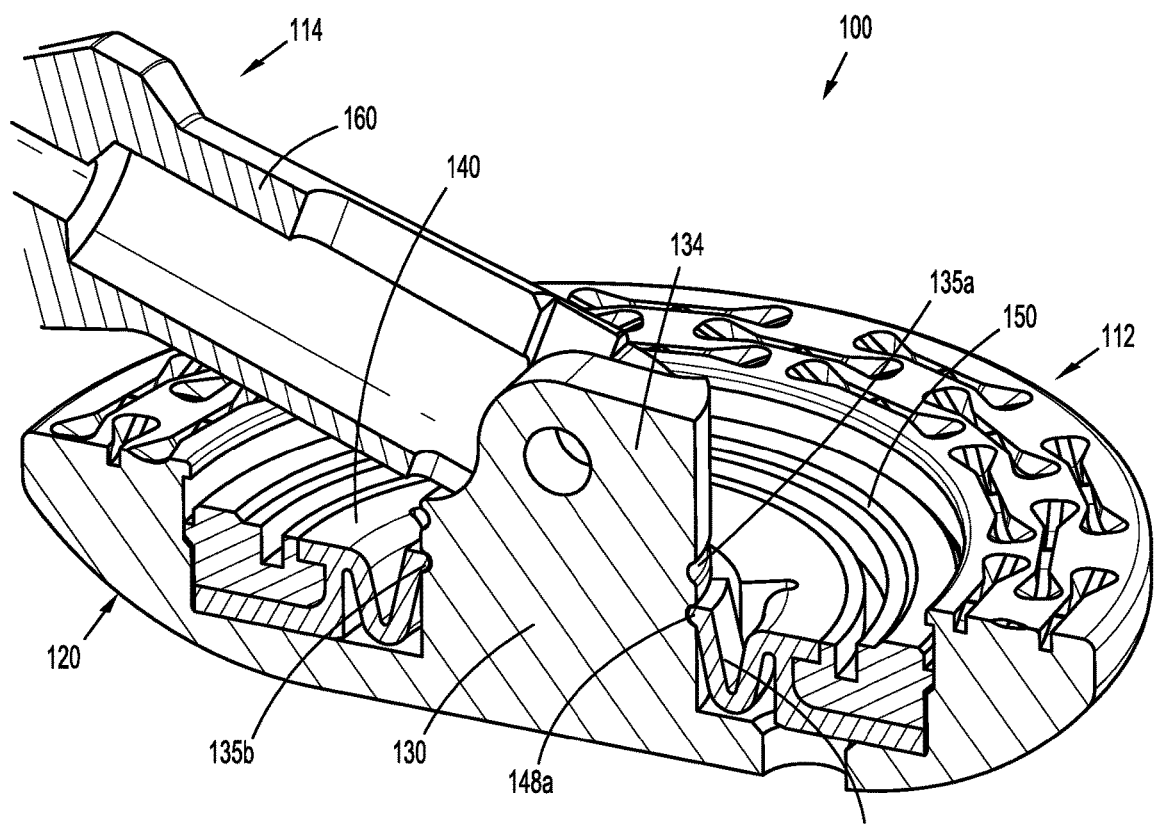
FIG. 12 is a cross-sectional perspective view taken along line 8-8 shown in FIG. 7 subsequent to tilting of the head assembly.
Figure 13:
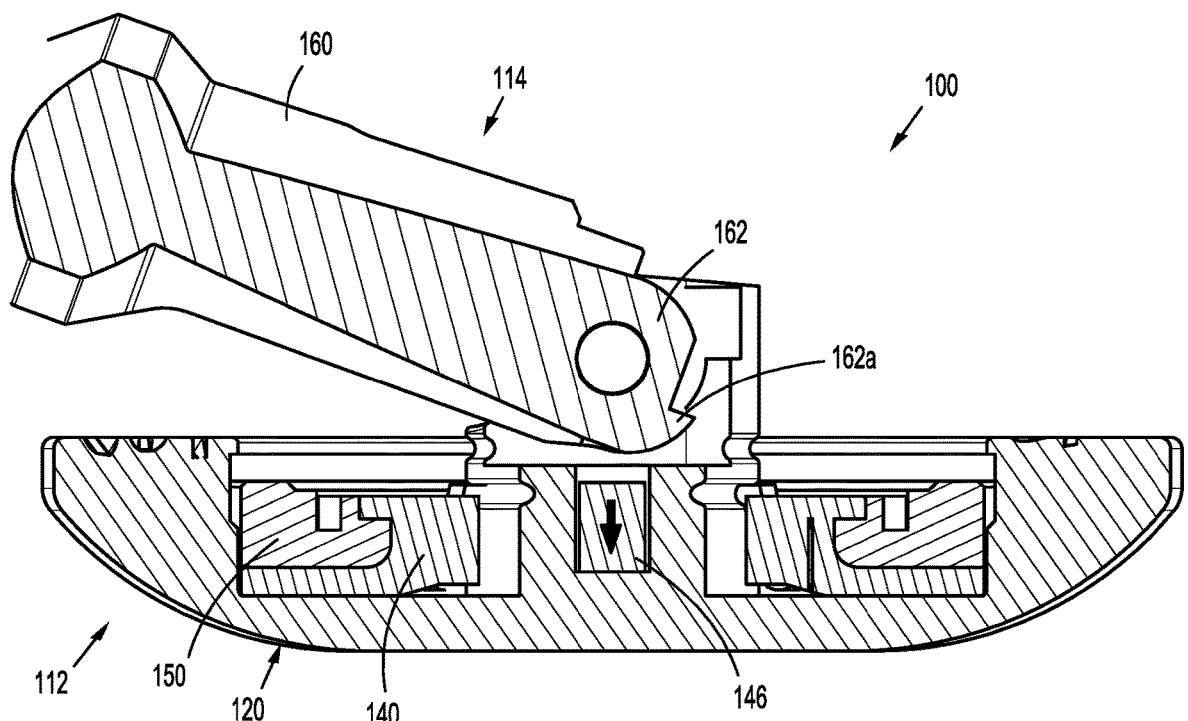
FIG. 13 is a cross-sectional side view taken along line 9-9 shown in FIG. 7, subsequent to tilting of the head assembly.

Turning now to FIGS. 11-13, the anvil assembly 100 is shown with the backup member 140 and the cutting ring 150 in the distal position. As the backup member 140 moves to the distal position, the opposed protrusions 144 of the backup member 140 disengage from the tabs 162a formed on the extensions 162 of the center rod 160 of the center rod assembly 114 to permit the head assembly 112 to pivot relative to the center rod assembly 114. As noted above, when the backup member 140 is in the distal position, the ridges 148a of the opposed locking features 148 align with and are received within the distal annular groove 135b of the post 130 to lock the backup member 140 in the distal position.

It is noted that the anvil head assembly 100 will not immediately tilt or pivot to the tilted position upon firing of the surgical stapling device 10 because, upon firing, the head assembly 100 is in an approximated position, i.e., the head assembly 100 is in close alignment with the loading unit 50 of the surgical stapling device 10 (FIG. 10). As such, the head assembly 100 is prevented from tilting until the head assembly 112 is moved away from the loading unit 50.

With reference to FIGS. 14-18, another embodiment of an anvil assembly according to the present disclosure is shown generally as anvil assembly 200. The anvil assembly 200 is substantially similar to the anvil assembly 100 described hereinabove and will only be described in detail as relates to the differences therebetween.

Figure 18:
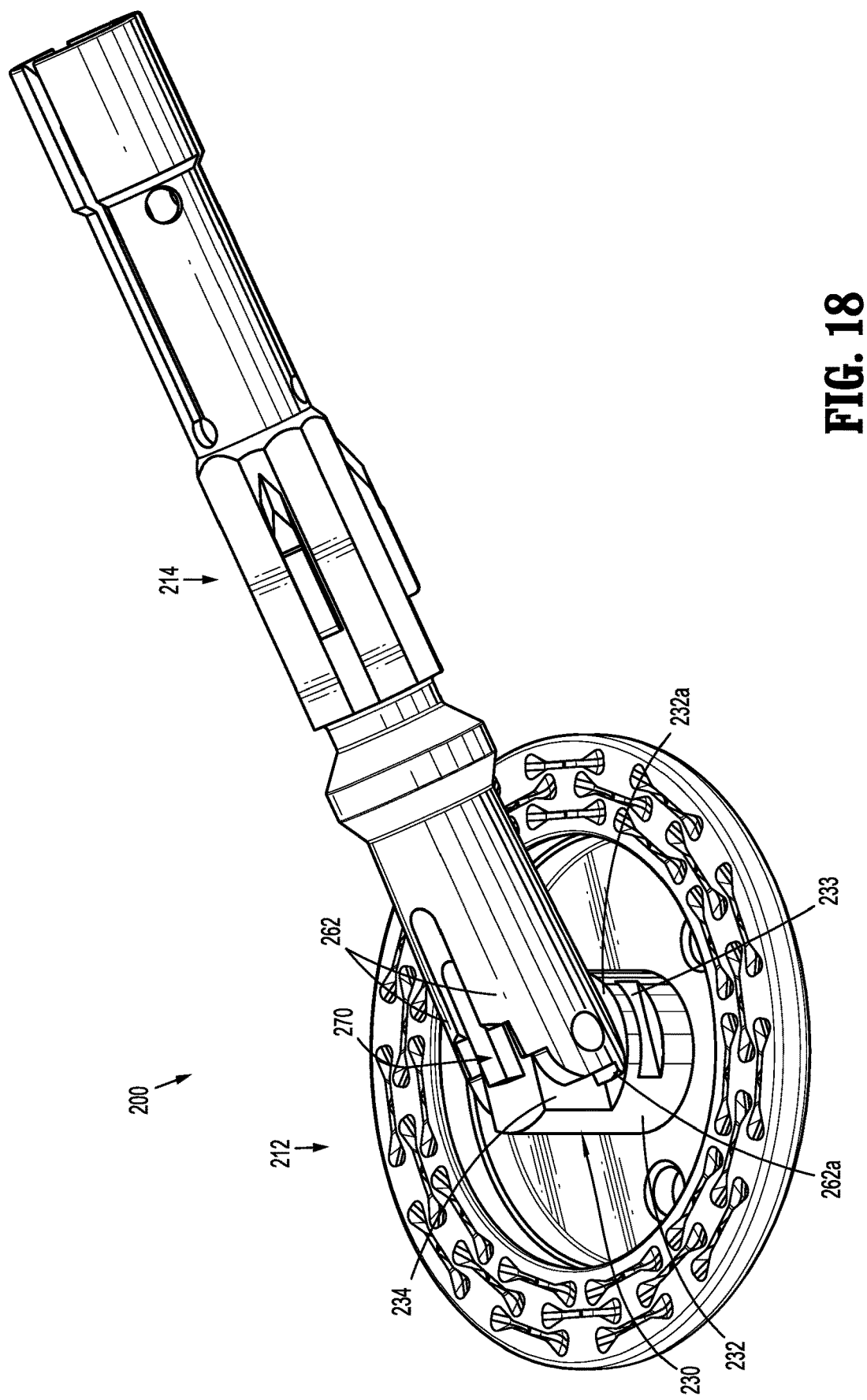
FIG. 18 is a perspective side view of the anvil assembly shown in FIG. 14 with the head assembly in a tilted position and the backup member and the cutting ring removed.

The anvil assembly 200 includes a head assembly 212 and a center rod assembly 214. The head assembly 212 includes a housing 220, a post 230, a backup member 240, and a cutting ring 250. The center rod assembly includes a center rod 260 and a biasing assembly 270 (FIG. 18). The housing 220 is substantially similar to housing 120 and will not be described any further herein.

Figure 17:
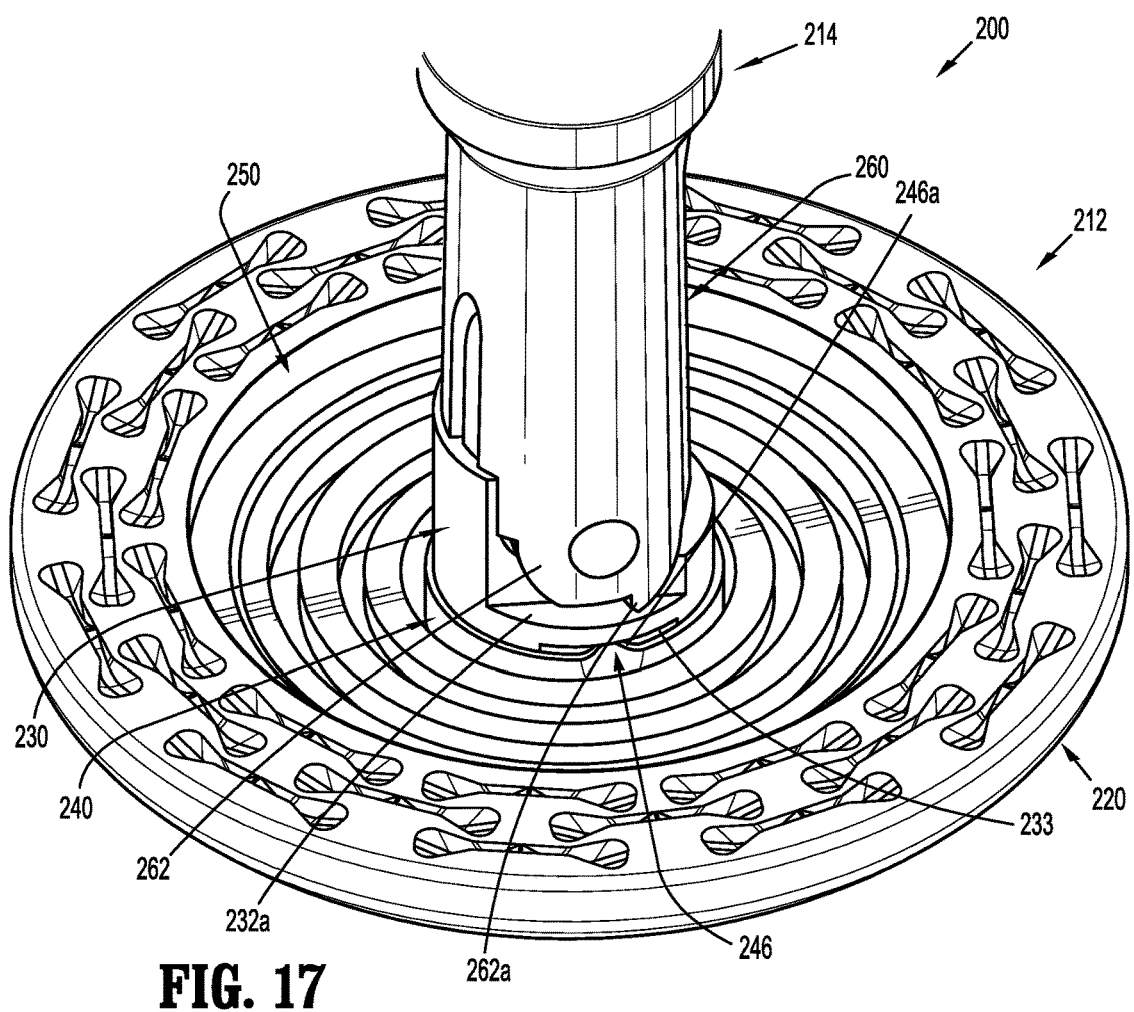
FIG. 17 is an enlarged perspective view of the head assembly of the anvil assembly shown in FIG. 14 with the backup member in a distal position.

The post 230 of the head assembly 212 is centrally disposed within the housing 220 and includes a substantially cylindrical body 232. A projection 234 extends proximally from the cylindrical body 232 and is pivotally secured to extensions 262 of the center rod 260. The cylindrical body 232 of the post 230 defines opposed cutouts 233. As will be described in further detail below, the opposed cutouts 233 facilitate securing the backup member 240 in a distal position (FIG. 17).

The backup member 240 includes a substantially planar body 242 and an annular flange 244 extending proximally from the planar body 242. The annular flange 244 is receivable about the post 230 and includes opposed detents 246 formed on a proximal end of the annular flange 244. The opposed detents 246 operate to maintain the backup member 240 in the proximal position prior to actuation of the surgical stapler 10 (FIG. 1) and in the distal position subsequent to actuation of the surgical stapler 10. The opposed detents 246 further operate to maintain the head assembly 212 in the operative position when the backup member 240 is in the proximal position. Although shown including two detents 246, it is envisioned that the backup member 140 may include three (3) or more detents 246.

The backup member 240 includes a plurality of tangs 248 for securing the cutting ring 250 to the backup member 240. Although shown including a plurality of tangs 248, it is envisioned that the cutting ring 250 may be secured to the backup member 240 in any suitable manner. The cutting ring 250 is substantially similar to the cutting ring 150 described hereinabove and will not be described in further detail herein.

Figure 14:
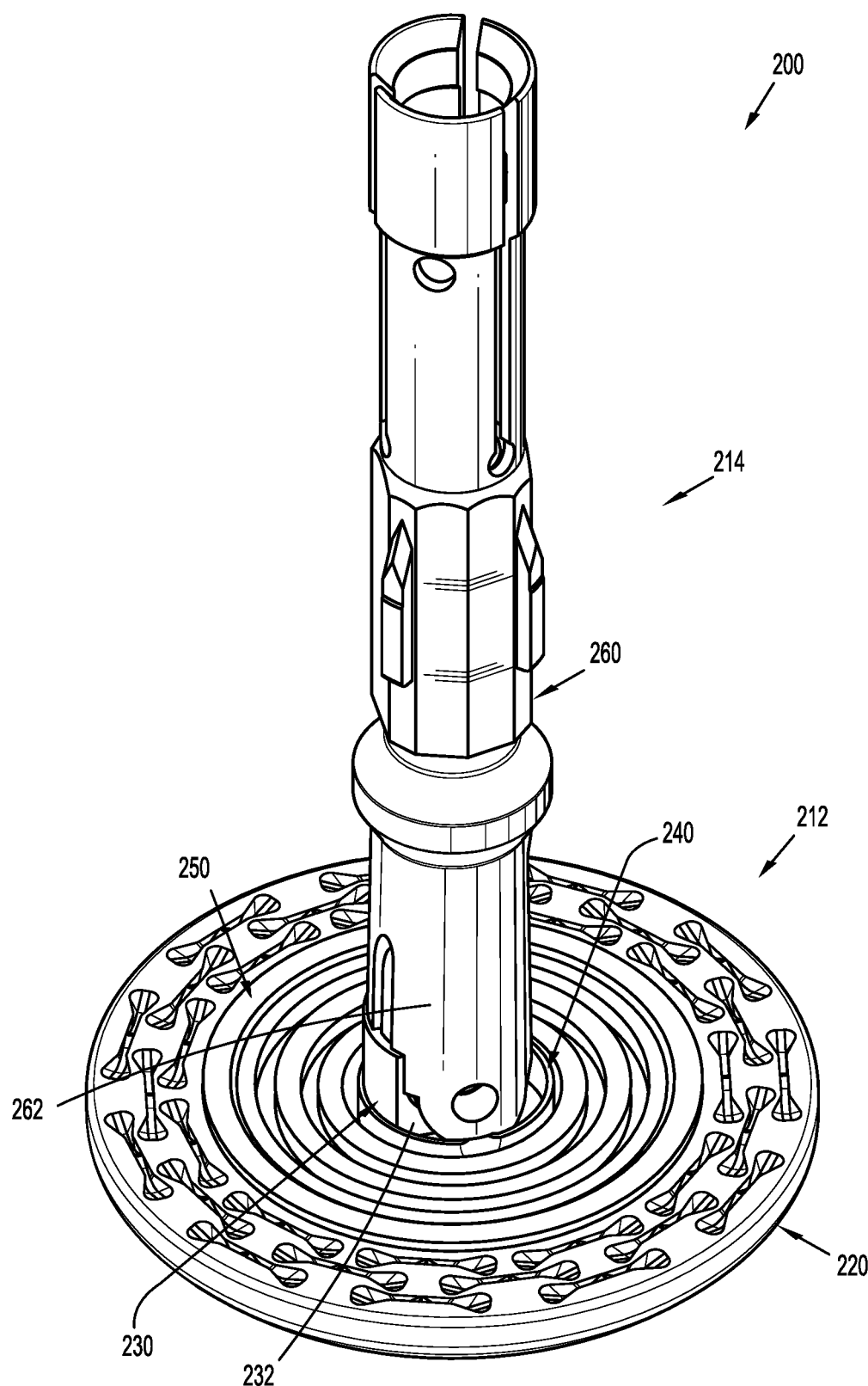
FIG. 14 is a perspective view of another embodiment of an anvil assembly according to the present disclosure.
Figure 15:
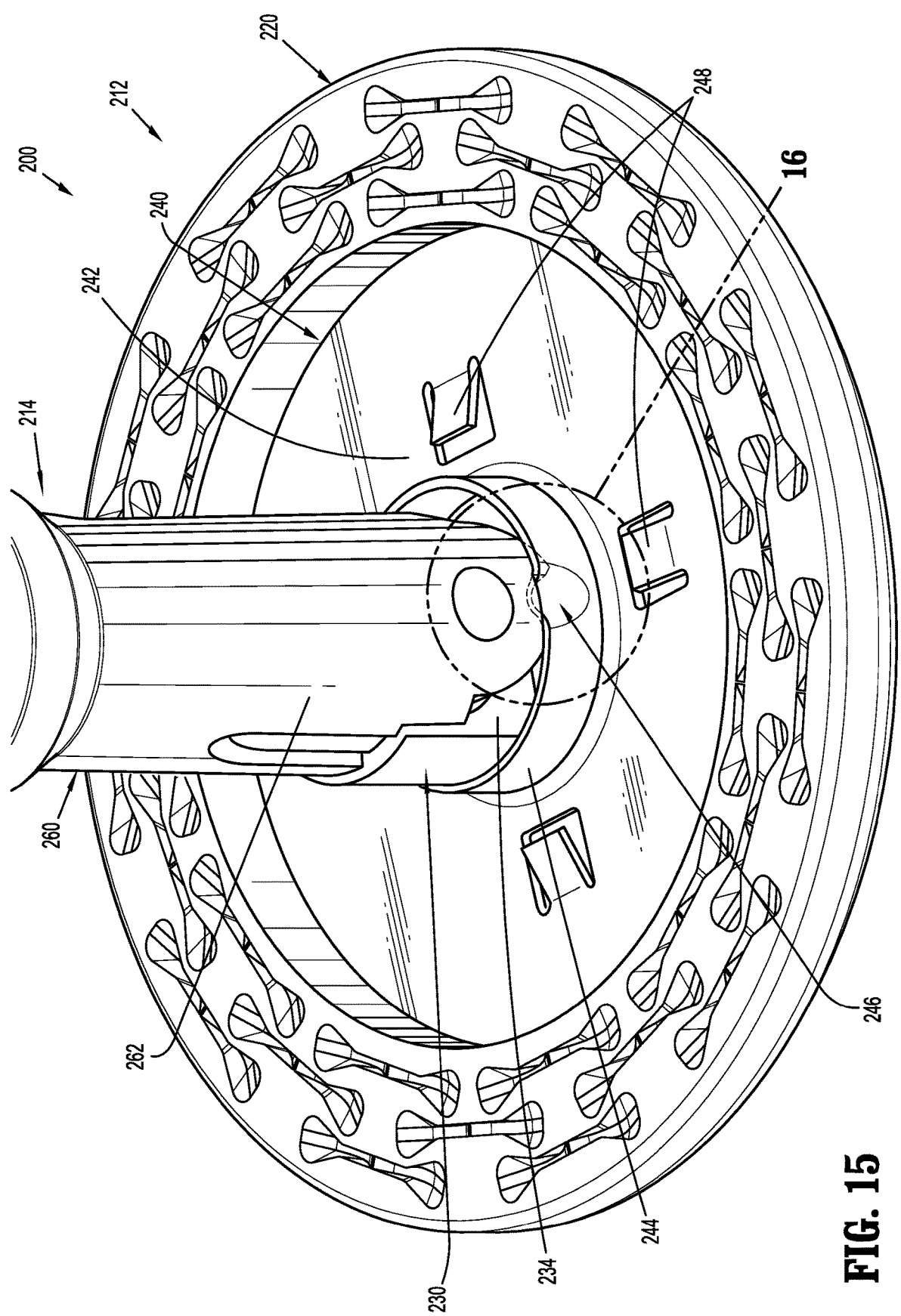
FIG. 15 is an enlarged perspective view a head assembly of the anvil assembly shown in FIG. 14 with a cutting ring removed and a backup member in a proximal position.
Figure 16:
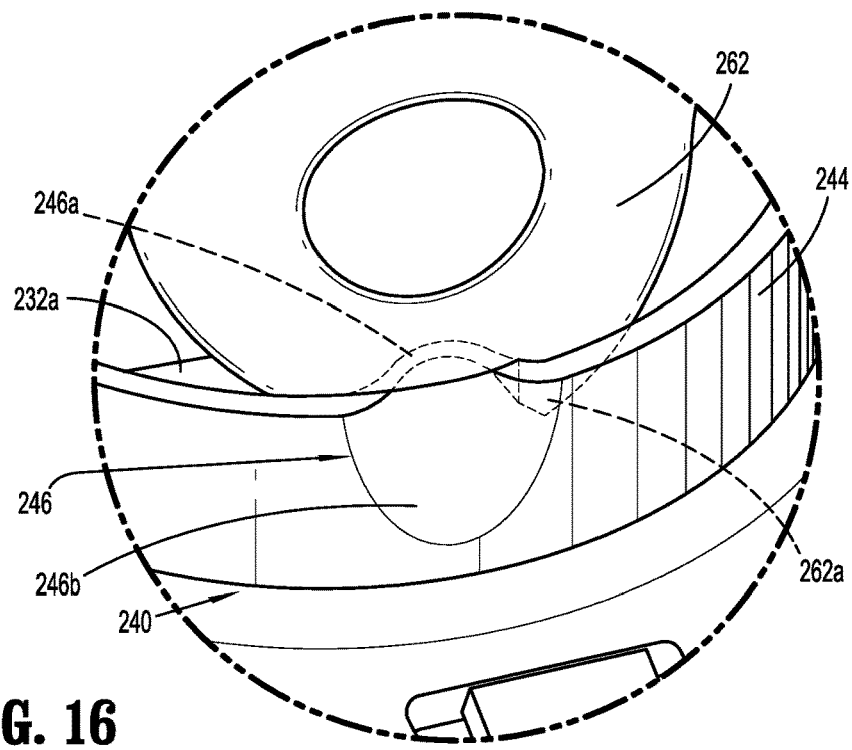
FIG. 16 is an enlarged view of the indicated area of detail shown in FIG. 15.

With reference to FIGS. 14-16, when the backup member 240 is in the proximal position, a distal portion 246*b* of the opposed detents 246 engages a top surface 232*a* (FIG. 16) of the cylindrical body 232 of the post 230 to maintain the backup member 240 in the proximal position. When the backup member 240 is in the proximal position, the opposed detents 246 are aligned with the tabs 262*a* formed on the extension 262 of the center rod 260 of the center rod assembly 214 to maintain the head assembly 212 in the operative position.

When a predetermined force is applied to the backup member 240, e.g., by knife 52 (FIG. 10) during actuation of the surgical stapler 10, the opposed detents 246 flex radially outwardly as the backup member 240 moves distally about the cylindrical body 232 of the post 230 to permit movement of the backup member 240 to the distal position. The post 230 may include a longitudinal slot (not shown) for receiving the detents 246 and facilitating distal movement of the backup member 240 from the proximal position to the distal position.

When the backup member 240 is in the distal position, the opposed detents 246 of the backup member 240 are received within the opposed cutout 233 of the post 230 to secure the backup member 240 in the distal position. More particularly, a proximal surface 246*a* of the opposed detents 246 engages the cylindrical body 232 of the post 230 when the detents 246 are received in the cutouts 233 of the post 230 to maintain the backup member 240 in the distal position.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. An anvil assembly comprising:
a center rod assembly including a center rod having at least one tab; and
a head assembly pivotally supported on the center rod assembly and moveable between an operative position and a tilted position, the head assembly including:
a housing;
a post extending proximally from the housing; and
a backup member operably supported about the post, wherein the backup member is movable from a first position in which a portion of the backup member is positioned to prevent pivotal movement of the head assembly from the operative position to the tilted position, to a second position in which the backup member is positioned to permit pivotal movement of the head assembly from the operative position to the tilted position, the backup member including at least one detent configured to engage a proximal surface of the post to maintain the backup member in the first position, wherein the at least one tab engages the backup member when the backup member is in the first position to maintain the head assembly in the operative position.

2. The anvil assembly according to claim 1, wherein the post defines at least a first cutout for receiving the at least one detent when the backup member is in the second position.

3. The anvil assembly according to claim 1, wherein movement of the backup member from the first position to the second position disengages the backup member from the at least one tab to permit the head assembly to move to the tilted position.

4. The anvil assembly according to claim 1, wherein the at least one tab engages the at least first detent.

5. The anvil assembly according to claim 1, wherein the at least one detent is configured to prevent movement of the backup member from the first position to the second position until a predetermined force is applied to the backup member.

6. The anvil assembly according to claim 1, wherein the at least one tab includes first and second tabs, and the at least one detent includes first and second detents.

7. The anvil assembly according to claim 1, wherein the post includes a top surface and the at least one detent includes a distal portion, the distal portion of the at least one detent engaging the top surface of the post when the backup member is in the first position to maintain the backup member in the first position.

8. An anvil assembly comprising:
a center rod assembly including a center rod having at least one tab; and a head assembly pivotally supported on the center rod assembly and moveable between an operative position and a tilted position, the head assembly including:
a housing;
a post extending proximally from the housing; and
a backup member operably supported about the post, wherein the backup member is movable from a first position in which a portion of the backup member is positioned to prevent pivotal movement of the head assembly from the operative position to the tilted position, to a second position in which the backup member is positioned to permit pivotal movement of the head assembly from the operative position to the tilted position, the backup member including at least one detent configured to engage a proximal surface of the post to maintain the backup member in the first position, wherein the at least one detent engages the post when the backup member is in the first position to maintain the backup member in the first position.

9. The anvil assembly according to claim 8, wherein the post defines at least a first cutout for receiving the at least one detent when the backup member is in the second position.

10. The anvil assembly according to claim 8, wherein movement of the backup member from the first position to the second position disengages the backup member from the at least one tab to permit the head assembly to move to the tilted position.

11. The anvil assembly according to claim 8, wherein the at least one tab engages the at least one detent.

12. The anvil assembly according to claim 8, wherein the at least one detent is configured to prevent movement of the backup member from the first position to the second position until a predetermined force is applied to the backup member.

13. The anvil assembly according to claim 8, wherein the at least one tab includes first and second tabs, and the at least one detent includes first and second detents.

14. The anvil assembly according to claim 8, wherein the post includes a top surface and the at least one detent includes a distal portion, the distal portion of the at least one detent engaging the top surface of the post when the backup member is in the first position to maintain the backup member in the first position.

15. A surgical stapling device comprising:
an actuation assembly including a trocar member; and
an anvil assembly releasably securable to the trocar member, the anvil assembly including:
a center rod assembly including a center rod having at least one tab; and
a head assembly pivotally supported on the center rod assembly and moveable between an operative position and a tilted position, the head assembly including:
a housing;
a post extending proximally from the housing; and
a backup member operably supported about the post, wherein the backup member is movable from a first position in which a portion of the backup member is positioned to prevent pivotal movement of the head assembly from the operative position to the tilted position, to a second position in which the backup member is positioned to permit pivotal movement of the head assembly from the operative position to the tilted position, the backup member including at least one detent configured to engage a proximal surface of the post to maintain the backup member in the first position, wherein the at least one tab engages the backup member when the backup member is in the first position to maintain the head assembly in the operative position.

16. The surgical stapling device according to claim 8, wherein the post defines at least a first cutout for receiving the at least one detent when the backup member is in the second position.

17. The surgical stapling device according to claim 15, wherein movement of the backup member from the first position to the second position disengages the backup member from the at least one tab to permit the head assembly to move to the tilted position.

18. The surgical stapling device according to claim 15, wherein the at least one tab engages the at least one detent.

19. The surgical stapling device according to claim 15, wherein the at least one detent is configured to prevent movement of the backup member from the first position to the second position until a predetermined force is applied to the backup member.

20. The surgical stapling device according to claim 15, wherein the at least one tab includes first and second tabs, and the at least one detent includes first and second detents.

* * * * *